United States Patent
Villain et al.

(10) Patent No.: US 9,251,593 B2
(45) Date of Patent: Feb. 2, 2016

(54) MEDICAL IMAGING SYSTEM AND A METHOD FOR SEGMENTING AN OBJECT OF INTEREST

(75) Inventors: Nicolas Villain, Clamart (FR); Claude Cohen-Bacrie, New York, NY (US); Jean-Michel LaGrange, Moissy Cramayel (FR); Claire Levrier, Rueil Malmaison (FR); Robert Randall Entrekin, Kirkland, WA (US)

(73) Assignee: Koninklijke Philips N.V., Eindhoven (NL)

( * ) Notice: Subject to any disclaimer, the term of this patent is extended or adjusted under 35 U.S.C. 154(b) by 2366 days.

(21) Appl. No.: 10/550,344

(22) PCT Filed: Mar. 18, 2004

(86) PCT No.: PCT/IB2004/000949
§ 371 (c)(1),
(2), (4) Date: Sep. 22, 2005

(87) PCT Pub. No.: WO2004/086297
PCT Pub. Date: Oct. 7, 2004

(65) Prior Publication Data

US 2006/0270912 A1 Nov. 30, 2006

(30) Foreign Application Priority Data

Mar. 27, 2003 (FR) ...................................... 03 50072

(51) Int. Cl.
*A61B 5/05* (2006.01)
*G06T 7/00* (2006.01)

(52) U.S. Cl.
CPC ............. *G06T 7/0081* (2013.01); *G06T 7/0091* (2013.01); *A61B 2576/00* (2013.01); *G06T 2207/10132* (2013.01);

(Continued)

(58) Field of Classification Search
USPC .................................. 600/407, 437; 382/128
See application file for complete search history.

(56) References Cited

U.S. PATENT DOCUMENTS 5,170,347 A 12/1992 Tuy et al.
6,389,310 B1 * 5/2002 Demonceau et al. ......... 600/512

(Continued)

FOREIGN PATENT DOCUMENTS

WO 0229719 A2 4/2002

OTHER PUBLICATIONS

Mc Inerney et al, "Deformable Models in Medical Image Analysis: A Survey", Medical Image Analysis, vol. 1, No. 2, 1996, pp. 91-108.

(Continued)

*Primary Examiner* — Jonathan Cwern

(57) ABSTRACT

The invention concerns a medical imaging system comprising means (4) of segmenting a region of interest around an object of interest within a volume of 3D data (3DV). The system according to the invention comprises means (5) of calculating a sub-regions map (CSR) within the segmented region (RS) and correction means (6) intended to exclude sub-regions of the segmented region by means of said sub-regions map (CSR). The correction can be made automatically or manually by means of control means (7) enabling a user to select the sub-regions to be excluded. Display means (3) make it possible to display a 2D representation (2DR) of the volume of 3D data (3DV) and the segmented region (RS, RS') at various stages of the processing.

20 Claims, 8 Drawing Sheets

Figure 1:
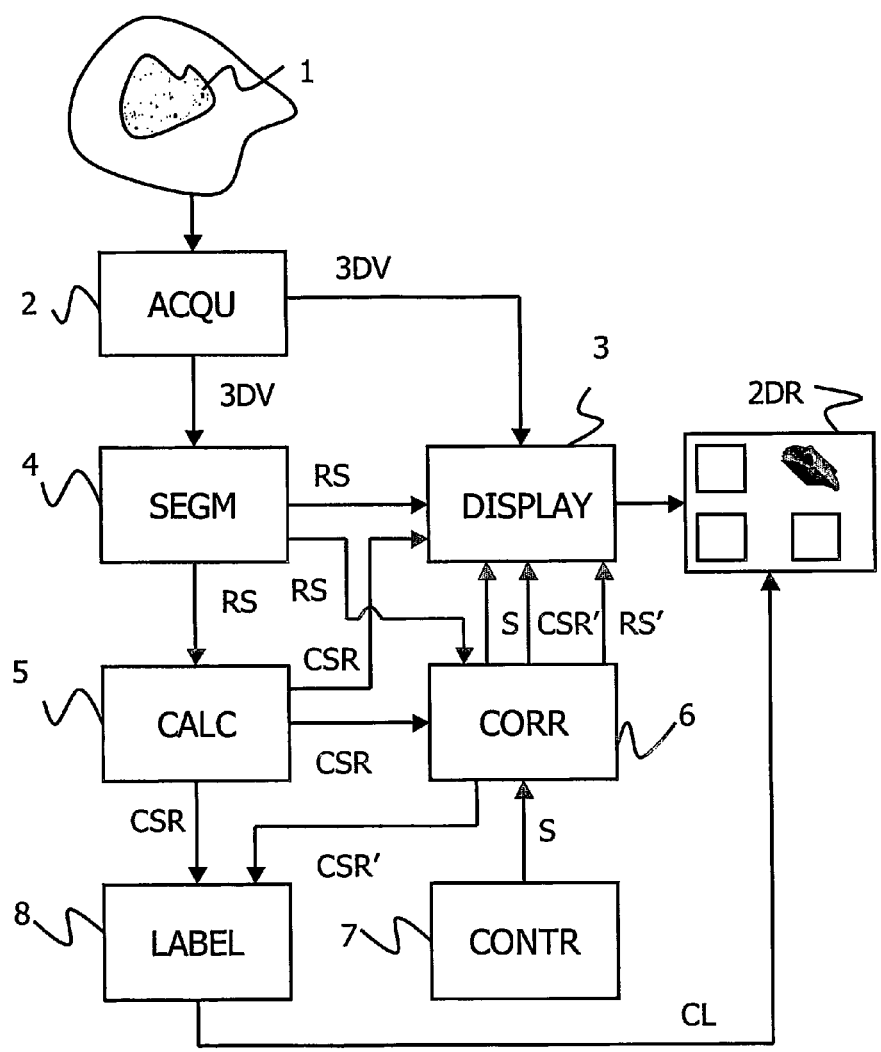

(52) U.S. Cl.
CPC ............... *G06T 2207/20132* (2013.01); *G06T 2207/20152* (2013.01); *G06T 2207/30004* (2013.01)

(56) References Cited

U.S. PATENT DOCUMENTS

| | | | | |
|---|---|---|---|---|
| 6,771,834 | B1* | 8/2004 | Martins et al. | 382/257 |
| 6,799,066 | B2* | 9/2004 | Steines et al. | 600/407 |
| 6,902,935 | B2* | 6/2005 | Kaufman et al. | 436/63 |
| 7,260,248 | B2* | 8/2007 | Kaufman et al. | 382/128 |
| 8,653,122 | B2 | 2/2014 | Savola et al. | |
| 2002/0007122 | A1* | 1/2002 | Kaufman et al. | 600/476 |
| 2002/0127735 | A1* | 9/2002 | Kaufman et al. | 436/172 |
| 2002/0197728 | A1* | 12/2002 | Kaufman et al. | 436/164 |
| 2003/0207250 | A1* | 11/2003 | Kaufman et al. | 435/4 |
| 2004/0022447 | A1* | 2/2004 | Mukhopadhyay et al. | 382/243 |
| 2004/0106868 | A1* | 6/2004 | Liew et al. | 600/442 |
| 2004/0153079 | A1* | 8/2004 | Tsougarakis et al. | 606/77 |
| 2005/0058322 | A1* | 3/2005 | Farmer et al. | 382/103 |
| 2005/0064602 | A1* | 3/2005 | Kaufman et al. | 436/164 |
| 2005/0168460 | A1* | 8/2005 | Razdan et al. | 345/419 |
| 2006/0270912 | A1* | 11/2006 | Villain et al. | 600/300 |

OTHER PUBLICATIONS

N. Ezquerra et al, "Knowledge-Guided Segmentation of 3D Imagery", CVGIP Graphical Models and Image Processing, vol. 58, No. 6, Nov. 1996, pp. 510-523, XP004418963.
J.A. Sethian, "Level Set Methods and Fast Marching Methods", published by Cambridge University Press in 1999, pp. 86-100.
Jan Sijbers, et al: Watershed-Based Segmentation of 3D MR Data for Volume Quantization, vol. 15, No. 6, 1997, pp. 679-688.

* cited by examiner

MEDICAL IMAGING SYSTEM AND A METHOD FOR SEGMENTING AN OBJECT OF INTEREST

The present invention relates to a medical imaging system intended to display and segment an object of interest within a volume of digital data in three-dimensions, referred to as 3D hereinafter. It also relates to a device intended to be integrated in such a system. It also relates to a medical imaging apparatus comprising such a system. It also relates to a method implemented by such a system. Finally, it relates to a computer program implementing such a method.

It finds in particular its application in the medical field, in particular for ultrasonic imaging.

3D imaging systems have been greatly developed over the past few years, including in the medical field. Consequently a doctor is more and more able to establish a diagnosis, for example to seek an object of interest, within a volume of 3D data, a 2D representation of which he displays on a screen. Such a volume comprises more information than a simple 2D image and makes it possible to detect objects of interest which are not very detectable on a 2D image. On the other hand, it is also more difficult to manipulate. This is because, unlike an image, not all the data are available simultaneously on a single 2D representation of the volume. The doctor must navigate in the volume and display several different 2D representations, for example views in section and/or views in perspective, of this volume. He therefore requires increased time to scan the volume exhaustively and establish his diagnosis.

There exist various techniques of automatic segmentation of the object of interest. The aim of such techniques is to save time for the doctor by revealing the object of interest but in no circumstances substituting itself for his diagnosis. In addition, the data acquired being complex and disturbed by the presence of noise, the segmentation obtained often comprises errors, which it is up to the doctor to correct from the 2D representation of the volume of data available to him.

U.S. Pat. No. 5,170,347 describes in particular an interactive procedure for dividing up an object of interest in three dimensions from a view of this object in perspective or 2D cross-sections. The user must define a 3D sub-region by tracing segments of curves which serve to form cross-section surfaces. A major drawback of this technique is that the user is required to manually draw segments which follow the contours of the sub-region to be divided up in a perspective view, whilst making the effort to imagine what will be the result in 3D.

However, though it is relatively simple to trace a contour on a 2D image, it is much more complicated to depict the surface formed from an intersection of several contours coming from different cross-sections. As for the trace of the cross-sectional surface directly on the perspective view, this is a tricky operation which requires the user to rotate the object of interest at the same time as he selects points belonging to this object. In addition, the user can define the cross-sectional surface only from points belonging to the surface rather than to the interior of the object of interest. A cross-sectional surface which is arbitrarily flat in pieces is therefore formed. Finally, in order to define precisely a cross-sectional surface which follows a complex object shape, the user must choose a large number of points. It can therefore be expected for the technique described in the prior art to be tedious and difficult to implement.

It is an object of the present invention to propose a simpler more rapid solution for correcting an automatic segmentation of an object of interest in a volume of 3D data, in particular in the medical field.

This aim is achieved by a medical imaging system comprising:
  acquisition means intended to acquire a volume of 3D digital data comprising at least one object of interest,
  means for segmenting a region of interest comprising said object of interest within said volume,
  means for displaying a 2D representation of said volume and said segmented region of interest,
  means for calculating a sub-regions map within said segmented region,
  correction means intended to exclude sub-regions from said region of interest by means of said sub-regions map.

The system according to the invention supplies a segmented region of interest comprising the object of interest. A user, for example a doctor, displays a 2D representation of the volume of data revealing the segmented region of interest. For example, said 2D representation comprises an image in perspective of a 3D reconstruction of the region of interest and at least two orthogonal cross-sections of the volume of data on which the contours of the segmented region are emphasized. The segmented region of interest is divided into sub-regions, which are for example signaled on the 2D representation by zones of different colors. The system makes it possible to make a correction to the segmented region by selecting the sub-regions to be excluded. Such a selection can be made automatically based on criteria related to the shape or position of the segmented region in the volume of data. It is a case for example of detecting protrusions. The selection can also be made manually or semi-automatically. In this case a user must select, for example by clicking, the sub-regions which he wishes to exclude from the segmented region, because he judges that they do not form part of the object of interest. The 2D representation is then updated in order to take into account the correction made by the user.

One advantage of the system according to the invention is to predefine the sub-regions to be excluded from the segmented region of interest. Consequently the user does not need to draw curve segments in a three-dimensional space. On the contrary, he is guided in his selection and can predict the effect of his corrective action since he knows in advance the form of the sub-region which he is selecting. This selection can be made equally well on 2D sections and on the image in perspective of a 3D reconstruction of the segmented region. The result of the correction is immediately visible on the updated 2D representation.

The invention will be further described with reference to examples of embodiments shown in the drawings to which, however, the invention is not restricted.

Figure 2:
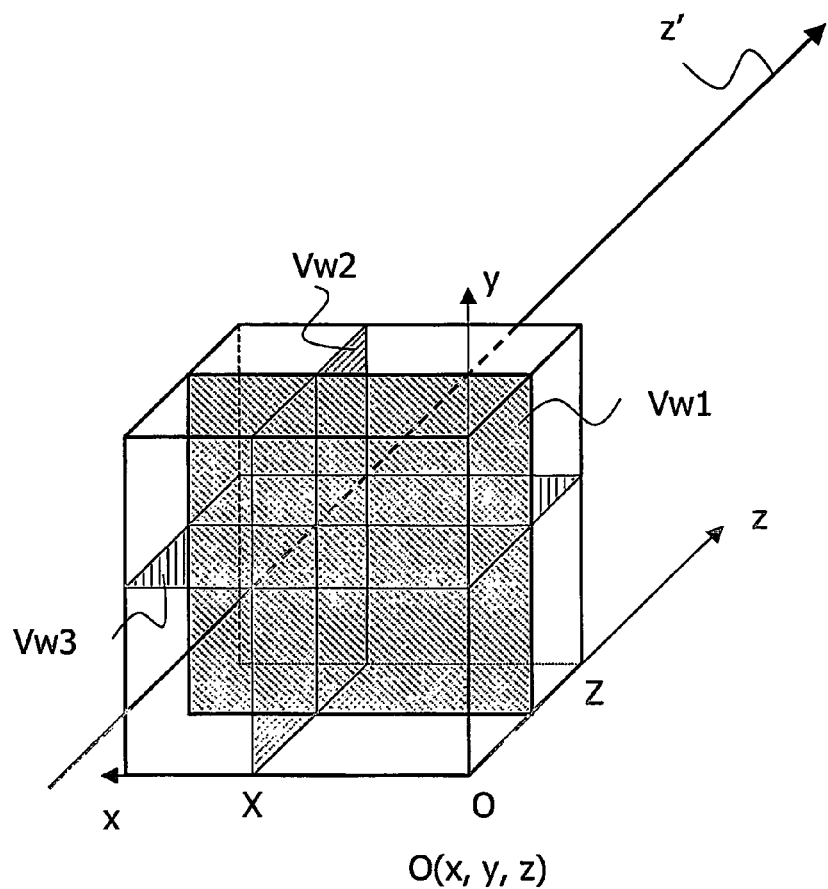
Figure 3A:
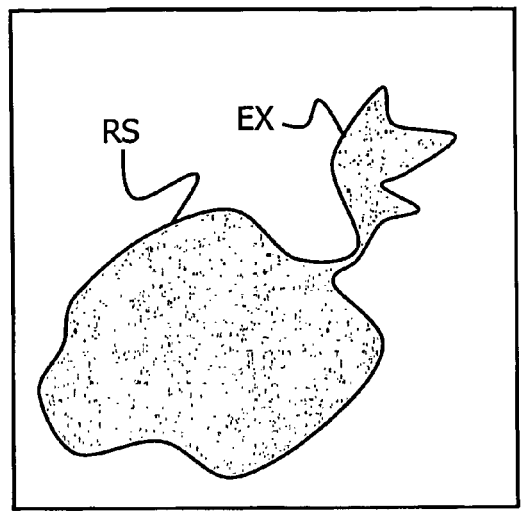
Figure 3B:
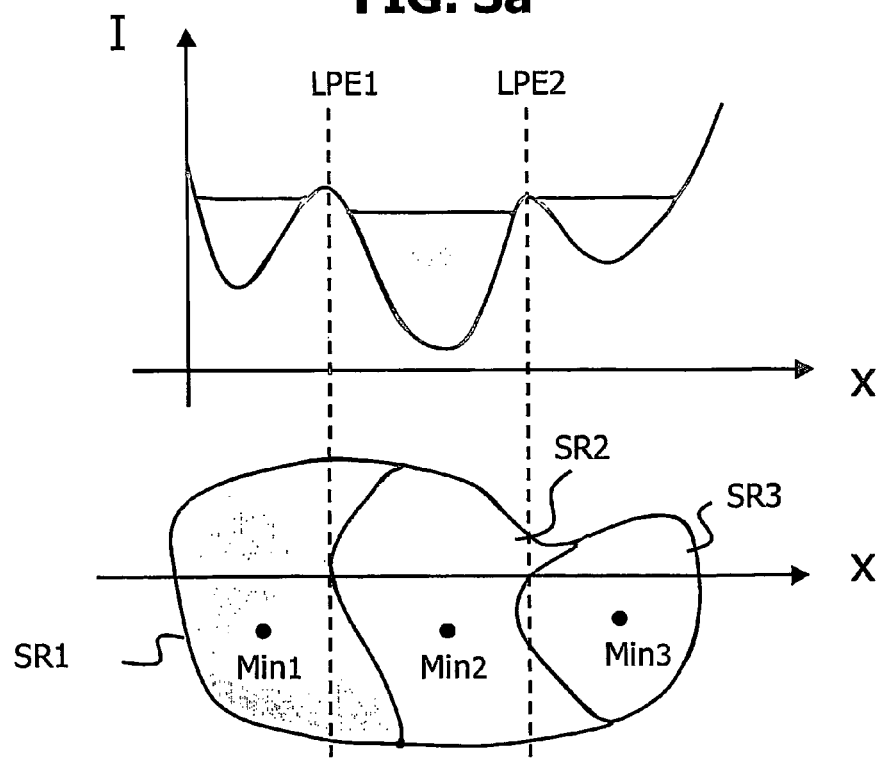
Figure 4:
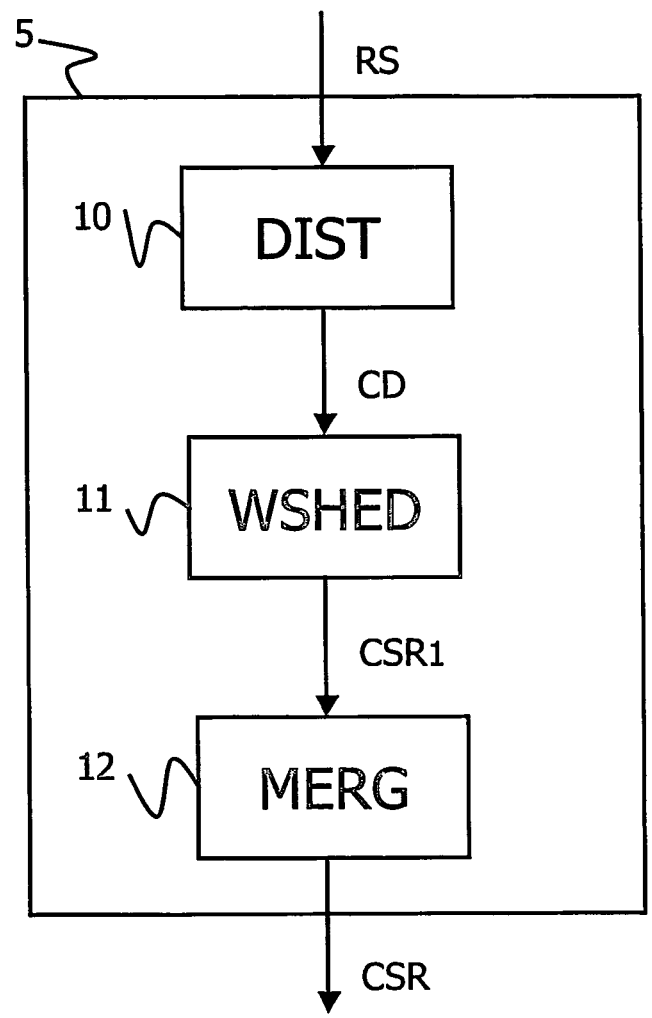
Figure 5:
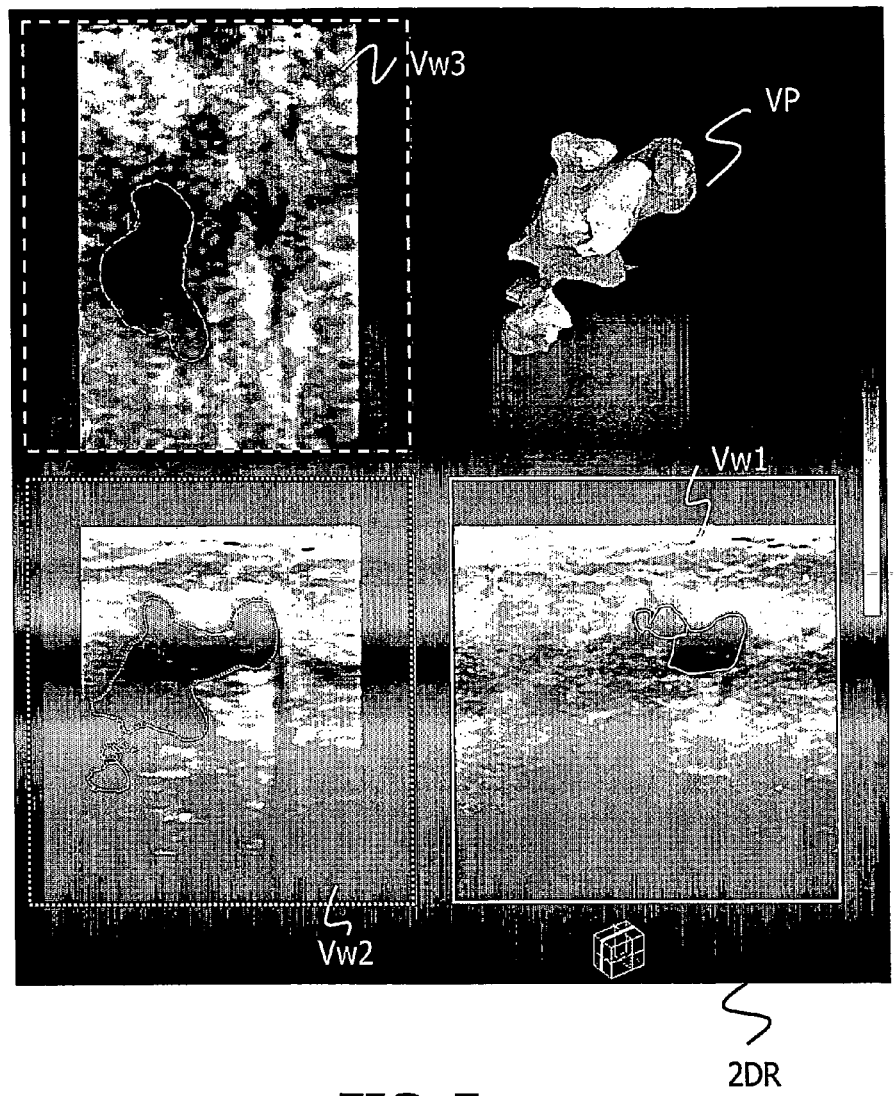
Figure 6:
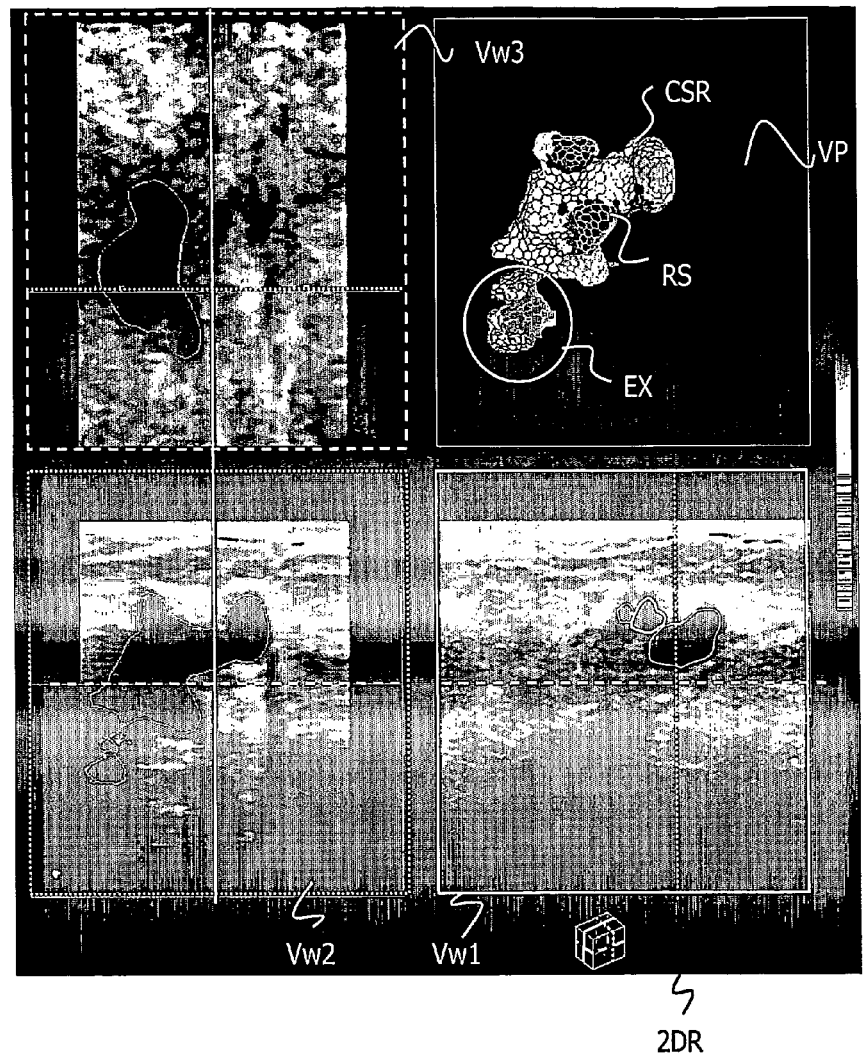
Figure 7:
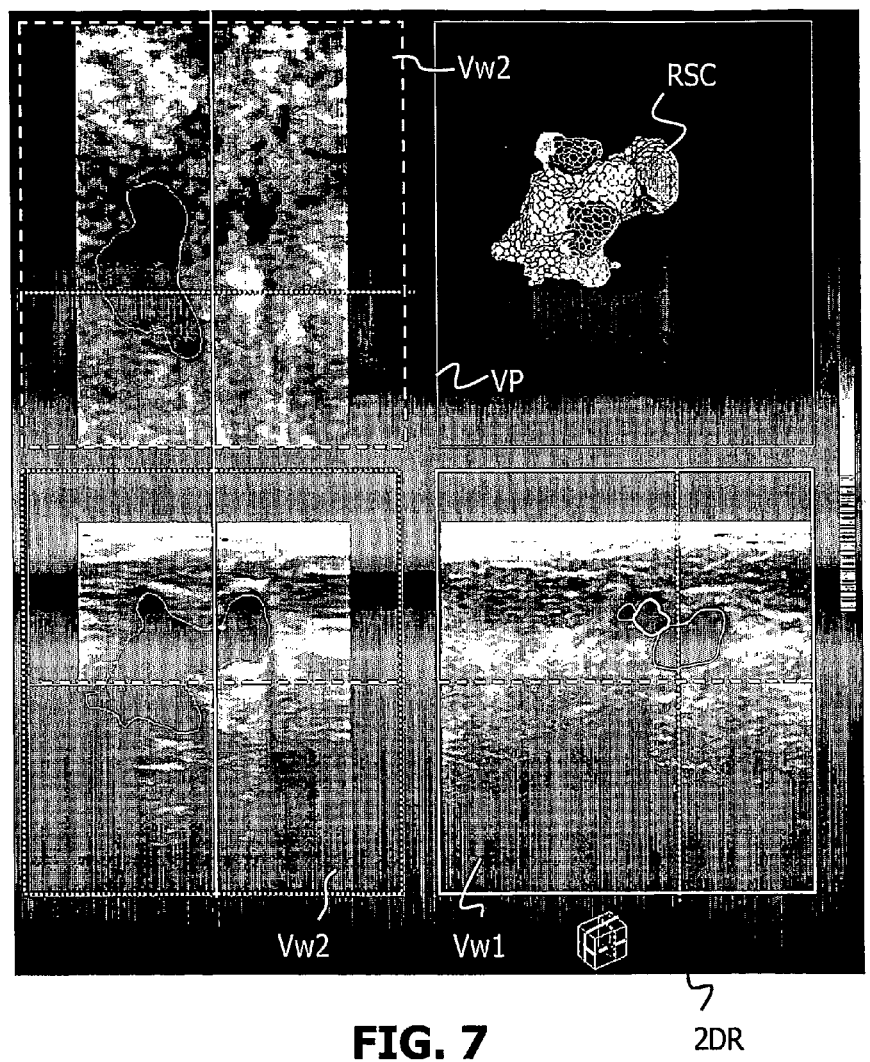
Figure 8:
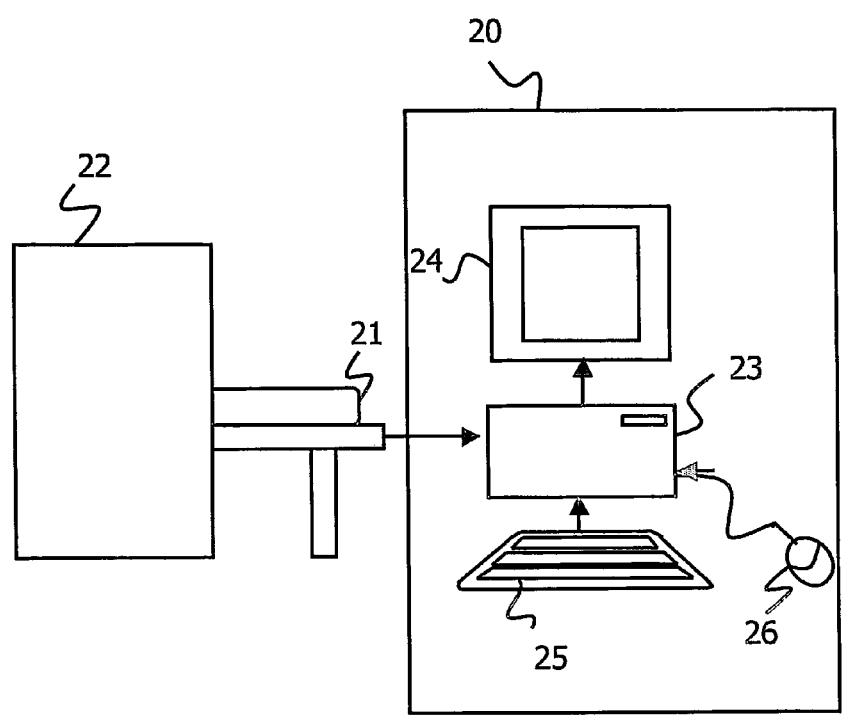

FIG. 1 presents a functional diagram of a medical imaging system according to the invention, FIG. 2 illustrates a volume of data referenced by a reference frame (O, x, y, z) and a possible choice of a display axis and of three orthogonal views for constructing a 2D representation of the volume of data according to the invention, FIG. 3a presents an example of a protrusion on a segmented region of interest, FIG. 3b illustrates the principle of the technique of calculating the watershed lines, FIG. 4 presents a functional diagram of the cutting means of the imaging system according to the invention, FIG. 5 presents an example of a 2D representation comprising three orthogonal views and a perspective view of a segmented region according to the invention, FIG. 6 presents an example of a 2D representation comprising three orthogonal views and a perspective view of a segmented region on which the sub-region map has been superimposed by means of color zones, FIG. 7 presents an example of a 2D representation obtained after correction of the segmented region, FIG. 8 depicts an outline diagram of a medical imaging apparatus according to the invention.

FIG. 1 depicts a functional diagram of a medical imaging system according to the invention. Such a system comprises acquisition means 2 intended to acquire a volume of 3D digital data 3DV formed by image formation means from a response of an environment to a signal. For example, the image formation means consist of an echographic probe intended to image part of the human body, according to a principle known to persons skilled in the art.

The medium is assumed hereinafter to contain at least one object of interest 1.

In a first embodiment of the invention, an ultrasonic imaging system used for displaying a breast lesion is considered. However, the invention is not limited to this particular case but can apply to the segmentation of any other type of object of interest in a volume of 3D digital data.

It is a case of segmenting, in the volume of data 3DV, a sub-volume of data corresponding to the object of interest 1. Hereinafter the complement of this sub-volume will be referred to as the "background", by analogy with a 2D image. The volume of data 3DV is referenced in space by a reference frame (O, x, y, z) as illustrated by FIG. 2. To any point $(x_0, y_0, z_0)$ of the volume 3DV there corresponds an intensity value $I(x_0, y_0, z_0)$.

The system according to the invention comprises segmentation means 4 intended to supply a segmentation of a region of interest comprising the object of interest 1. It is a case in fact of detecting the contours of the object of interest in the volume 3DV. Several segmentation techniques, known to persons skilled in the art, can be used. In the first embodiment a region growth technique is applied. Such a technique is in particular described on pages 313 and 314 of the document by K. R. Castelman entitled "Digital Image Processing" published by Prentice Hall in 1979. Its principle is as follows: a region to be segmented in the volume 3DV comprises points which can advantageously by characterized by a characteristics vector. Such a vector comprises for example the value of the intensity and measurements describing a texture around this point, such as measurements of contrast, correlation, homogeneity or entropy. A particular point in the region to be segmented is designated by a user. The region growth technique consists of considering a vicinity of points around the designated point and comparing the values of their characteristics vectors with those of the designated point. A point in the vicinity is associated with the designated point if its characteristics vector is sufficiently close to that of the designated point, that is to say if a distance measurement between these two vectors is below a predetermined threshold.

The operation is renewed for each point associated with the initially designated point, which has the effect of increasing a region around the initially designated point. The process stops when all the associated points have been tested. A segmented region RS is then obtained.

Said segmented region RS is located in the three-dimensional reference frame (O, x, y, z) associated with the volume of data 3DV. It is for example described by a three-dimensional table of points RS(x, y, z), such that a point $RS(x_0, y_0, z_0)$ receives a non-zero value if it forms part of the segmented region of interest RS. Advantageously, there is allocated to the point $(x_1, y_1, z_1)$ of the segmented region its intensity value $I(x_1, y_1, z_1)$ in the volume 3DV.

One advantage of such a technique is being relatively simple and supplying only one region. A drawback of this technique is giving rise to "leaks", that is to say by error making the region grow in one direction, from a zone where the boundary of the object of interest is distinguished less clearly from the background. Such leaks give rise to the formation of protrusions EX, such as that presented in FIG. 3a. The phenomenon of leaks is all the more probable when a higher threshold is chosen, that is to say points possessing more distinct characteristics are aggregated. On the other hand, the choice of a high threshold also makes it possible to form a segmented region containing the object of interest in its entirety.

It should be noted that the invention is not limited to the region growth technique mentioned above. By way of alternatives, other segmentation techniques can equally well be used. One of them is the "fast marching" technique which consists, from a point $P_0$ chosen by the user and a potential depending on the intensity at any point P in the volume 3DV, of calculating the propagation time of a wave from $P_0$ to P. To each time or time step there thus corresponds a position of a wave edge, which is a 3D surface, closed and continuous, separating an object of interest from the background. Such a technique is described in more detail on pages 86 to 100 of the book by J. A. Sethian entitled "Level Set Methods and Fast Marching Methods" published by Cambridge University Press in 1999.

Another technique is the active objects technique, which consists of making a 3D surface change under the effect of internal forces, dependent on the surface itself, and external forces dependent on the volume of data, until an equilibrium is reached. Such a technique is described in more detail in the document by McInerney, T. and Terzopoulos entitled "Deformable Models in Medical Image Analysis: A Survey", on pages 91 to 108 of the journal Medical Image Analysis, Vol. 1, N° 2, in 1996.

Whatever the case, the technique used supplies a segmentation of the object of interest which includes errors. This is because, in the medical field, an object of interest often has a relatively low contrast and visibility affected by the presence of noise and artifacts depending on the imaging method used. As mentioned previously, it is possible to act on the sensitivity of the segmentation technique used, so that the segmented region obtained (RS) entirely contains the object of interest.

Hereinafter a segmented region RS which contains the object of interest is therefore considered. It is then a case of correcting the segmented region RS so that it corresponds as precisely as possible to the boundaries of the object of interest.

To this end, the system according to the invention comprises means 5 for calculating a sub-region map within the segmented region (RS). A functional diagram of the calculation means 5 is presented in FIG. 4. In the first embodiment, the cutting means 5 according to the invention comprise sub-means 11 for calculating watershed lines. A basic principle of this technique is illustrated by FIG. 3b. FIG. 3b depicts a 1D profile I(x), in a direction x, of the intensity of a dark object of interest on a light background. The 1D profile presents three "bowls" which correspond to local minima $Min_1$, $Min_2$ and $Min_3$ of the intensity of the segmented region. It can be imagined filling these bowls with water. The content of a bowl will mix with that of an adjacent bowl at a boundary commonly referred to as the "watershed" by analogy with watercourses. In the example in FIG. 3b, the three bowls give rise to two watershed lines $LPE_1$ and $LPE_2$, which divide the segmented region into three sub-regions $SR_1$, $SR_2$ and $SR_3$. These three sub-regions are formed as follows:

there are allocated to the local minima $Min_1$, $Min_2$ and $Min_3$ labels corresponding respectively to the sub-regions $SR_1$, $SR_2$ and $SR_3$, for each local minimum $Min_i$, a vicinity $V_i$ is considered around this local minimum and the points in the vicinity $V_i$ to $Min_i$ are aggravated by allocating the label $SR_i$ to them, provided that they do not already belong to another region, the same procedure is followed for the other minima, the process is repeated on the neighbors which have just been aggregated, the process ends when all the points in the segmented region have received a label.

This principle easily extends to a volume of data such as the segmented region RS. In this case, the vicinity $V_i$ considered is for example cubic.

A first sub-regions map $CSR_1$ is obtained. In the case which has just been described the sub-regions map $CSR_1$ follows the variations in relief of the contrast of the segmented region.

In a second embodiment, the cutting means 5 also comprise sub-means 10 for calculating a distance map CD from the segmented region RS. Said sub-means 10 are able to calculate, for each point P of the segmented region RS, the shortest distance $D_{min}(P)$ which separates it from an edge of the segmented region RS and to allocate the opposite of this value $D_{min}(P)$ to the corresponding point P of the distance map CD. The distance map CD obtained comprises local minima at the places where the distance to the closest edge of the segmented region is at a maximum. It should be noted that the term distance map designates here a three-dimensional table $CD(x,y,z)$ such that, for a point $(x_2, y_2, z_2)$, $CD(x_2, y_2, z_2)$ is equal to the opposite of the distance from this point to the closest edge of the segmented region.

The sub-means 11 for calculating the watersheds is then applied to the minima of the distance map. The set of sub-regions obtained differs from the previous one in that the sub-regions are formed this time on the relief of the distance map instead of the relief of the contrast map. One advantage of the preferred embodiment is therefore to provide a division of the segmented region into morphological sub-regions whose boundaries are generated solely by the forms of the segmented region.

It should be noted that, in the majority of cases, an excessively large number of sub-regions is obtained. In the first embodiment, this is explained by the fact that the intensity values are often disturbed, which has the effect of creating a multitude of local minima and therefore a very fragmented sub-regions map. In the second embodiment, a similar phenomenon occurs, this time because the edges of the segmented region are often irregular in shape and give rise in their turn to a multitude of local minima within the distance map CD.

To remedy this, the calculation means 5 according to the invention comprise merging sub-means 10 intended to merge the sub-regions together so as to form a second sub-regions map CSR comprising a lesser number of sub-regions. In the second embodiment, the principle used is as follows:

an absolute minimum is sought amongst all the local minima of the distance map: it corresponds to a distance Dmax to the edges of the segmented region, all the other minima, situated at a distance less than Dmax and whose sub-region is related to that of the absolute minimum, are considered under the influence of the absolute minimum and their region is merged with that of the absolute minimum, the process is repeated until an equilibrium is achieved, that is to say sub-regions can no longer be merged.

By way of alternative, it is also possible to merge the regions which have a large part of their boundary in common or whose mean intensity is very close.

It should be noted however that it is possible to modulate the distance Dmax by a multiplying factor, so as to eliminate the sub-regions artificially created by the noise present in the volume of data 3DV, without for all that obtaining sub-regions which are too non-homogeneous.

The merging sub-means 12 make it possible to obtain a second sub-regions map CSR which is less divided, whose sub-regions actually have a direction and are in limited numbers. This is a real advantage for subsequent use of the said sub-regions map, for example in order to correct the segmented region.

The system according to the invention comprises display means 3 for displaying a representation 2DR of the volume of data 3DV and of the segmented region RS.

In the preferred embodiment, the representation 2DR comprises three orthogonal views $Vw_1$, $Vw_2$ and $Vw_3$ of the volume of data 3DV, which intersect each other on a display axis Oz'. For example, the view $Vw_1$ is orthogonal to the axis Oz' and the two views $Vw_2$ and $Vw_3$ pass through this axis, as shown by FIG. 2. An example of a representation 2DR is presented in FIG. 5. The intersections of the segmented region RS with the three views are highlighted on the representation 2DR by a color curve. The representation 2DR can also comprise a perspective view VP of the segmented region reconstructed in 3D, for example by a surface rendition technique known to persons skilled in the art. The sub-region map CSR is for example superimposed on the perspective view VP of the segmented region, for example by allocating a different color to each sub-region, as is the case in FIG. 6. It can also be superimposed on the views $Vw_1$, $Vw_2$ and $Vw_3$.

One advantage of this representation 2DR is to enable the user to display the segmented region RS and the sub-regions according to his preferences, that is to say either on the 2D views or on the perspective view.

The system according to the invention comprises control means 7 enabling the user to interact with said representation 2DR and in particular to navigate in the volume of data 3DV by choosing a position of the display axis z' and a depth Z of the view $VW_1$, as shown in FIG. 2.

The system according to the invention also comprises correction means 6 intended to exclude sub-regions of the segmented region of interest. In the first and second embodiments of the invention, the sub-regions to be excluded are selected manually by a user, who must interact with the representation 2DP. To this end, the control means 7 also enable the user to select a sub-region to be excluded, for example by clicking on a point on this sub-region. A selection S of sub-regions is supplied to the correction means 6. The correction means 6 are able to take into account the selection S and to supply a corrected segmented region RS' and sub-regions map CSR'. An example of a correction is presented in FIG. 7.

In a third embodiment, the decision on the sub-regions to be excluded is taken automatically, that is to say without the intervention of a user, using predefined criteria. These criteria are for example shape criteria, dependent on the object of interest and the application. In particular, in the medical field, there exist anatomical structure models which can be used for roughly fixing limits to the object of interest. Any sub-region exceeding these limits is then automatically eliminated. Likewise, during acquisition, the field of vision of the medical imaging apparatus is chosen so as to completely include the object of interest. Any sub-region reaching the edge of this field of view can also be automatically eliminated. It is also possible to reject a type of shape if it does not correspond to any anatomical reality, such as for example a protrusion, that is to say a sub-region which is connected to the others only by a narrow segment. In this case, for a given sub-region, it suffices to compare its total external surface SE and the surface SC of its boundary with the sub-regions which separate it from the starting point $P_0$ designated by the user for the initial segmentation. When the ratio SC/SE is less than a threshold fixed in advance, this means that this sub-region is the "neck" of a protrusion and can therefore be eliminated automatically. It should be noted that all the sub-regions are updated and that only the sub-regions connected to $P_0$ are kept.

The system according to the invention also comprises updating means intended to take into account the changes requested by the user and to recalculate a new representation 2DR.

In another embodiment of the invention, the correction means 6 are able to combine an automatic correction mode and a manual correction mode. For example, the results of the automatic correction are looked at by a user.

It should be noted that the display means make it possible to display the volume 3DV and possibly the segmented region at all stages of the processing, whether after acquisition of the volume 3DV, after the segmentation of the object of interest, after the division of the segmented region into sub-regions or after a first correction of the segmented region. Examples of representations 2DR at the various stages of processing are presented in FIGS. 5, 6 and 7.

In a fourth embodiment, the system according to the invention comprises labeling means 8, presented in FIG. 1, intended to label the sub-regions of the segmented region RS. It is a case for example of recognizing various constituent parts of an object of interest, such as two ventricles of the heart. The dividing means have supplied a sub-regions map CSR in which every point possesses the label of the sub-region to which it belongs. The labeling means 8 consist of associating with such a label a second label having this time a meaning, for example anatomical. A label map CL is delivered. This map is for example a simple one-dimensional table which allocates to a sub-region $SR_i$ a label $L_i = CL(SR_i)$.

Such means can also be implemented automatically, manually or semi-automatically. In automatic mode, this labeling can be carried out using a priori knowledge rules which define a model of the object of interest and its constituent parts. For example, in the case of the heart, certain anatomical structures, such as the valve plane or the apex, can be detected automatically in the volume of data or designated by an expert in a particular image and tracked automatically over time and/or as the patient moves or located roughly from an average anatomical model. Such anatomical structures constitute key anatomical reference points. The position of a sub-region with respect to such reference points determines whether it belongs to a given anatomical region and the corresponding label is automatically associated with it. In manual mode, a user who has selected a sub-region $SR_i$ is for example invited to choose a label $L_i$ from amongst a list of labels offered. Labeling is facilitated since it requires of the user no complex manipulation of the volume of data 3DV.

FIG. 8 presents an outline diagram of a medical imaging apparatus comprising an imaging system 20 according to the invention. Such an apparatus comprises a table 21 or any other element for installing a patient and means 22 of forming a volume of digital data from a response of an area of the body of the patient to a signal, for example echographic. The volume of digital data obtained is transmitted to the system 20 according to the invention. Such a system is for example implemented by a calculation unit 23 of a computer in software and/or hardware form. A 2D representation of the volume of data is displayed on a screen 24. The system according to the invention comprises control means which are for example used by means of a keyboard 25 or a mouse 26.

It is possible to implement the processing method according to the invention by means of a suitably programmed circuit. A computer program contained in a programming memory may cause the circuit to perform the various operations described previously with reference to FIG. 1. The computer program can also be loaded into the programming memory by reading a data medium such as for example a disk which contains said program. The reading can also take place by means of a communication network such as for example the Internet. In this case, a service provider will make the computer program available to interested parties in the form of a downloadable signal.

The invention is not limited to the embodiments which have just been described by way of example. Modifications or improvements can be made thereto whilst remaining within the scope of the invention. In particular, other imaging methods, such as magnetic resonance imaging or positron emission tomography, can be used.

In the present text, the verb "comprise" is used to signify that the use of other elements, means or steps is not excluded.

The invention claimed is:

1. A medical imaging system comprising:
    a memory that is configured to store data corresponding to a three-dimensional region of interest that includes at least one object of interest,
    a calculation unit that is configured to:
        identify a segment of interest corresponding to a contour of the object of interest, by identifying points in the segment of interest having similar characteristics based on the data,
        identify a plurality of sub-segments within the segment of interest, boundaries of the sub-segments being based on variations of at least one characteristic within the segment of interest, and
        remove select sub-segments from the segment of interest to form an other segment of interest corresponding to the contour of the object of interest, and
    a display unit that is configured to display the segment of interest, the boundaries of the sub-segments, and the other segment of interest.

2. The system of claim 1, wherein the boundaries of the sub-segments are determined by determining local minima and watersheds within the segment of interest.

3. The system of claim 2, wherein the at least one characteristic includes distances of the points in the segment from an edge of the segment.

4. The system of claim 1, wherein the at least one characteristic includes distances of the points in the segment from an edge of the segment.

5. The system of claim 1, wherein the at least one characteristic includes intensity values of the points in the segment.

6. The system of claim 1, including merging an initial plurality of sub-segments to form the plurality of sub-segments.

7. The system of claim 6, wherein the merging is based on distances of the points in the segment from an edge of the segment.

8. The system of claim 6, wherein the merging is based on intensity values of the points in the segment.

9. The system of claim 1, including a user interface that allows a user to identify one or more of the select sub-segments to remove based on the display of the segment of interest and the boundaries of the sub-segments.

10. The system of claim 1, wherein the display unit is configured to render a perspective view of the segment of interest and one or more boundaries of the sub-segments.

11. The system of claim 1, wherein the one or more boundaries are displayed by displaying the sub-segments in different color.

12. The system of claim 1, wherein at least one of the select sub-segments is removed based on a characteristic of the boundary of the sub-segment.

13. The system of claim 12, wherein the characteristic of the boundary includes a surface area of the boundary.

14. The system of claim 12, wherein the characteristic of the boundary includes a ratio of a surface area of the boundary to a surface area of the sub-segment.

15. The system of claim 1, including a medical imager that provides the three-dimensional (3D) digital data.

16. The system of claim 1, wherein the similar characteristics include measures of intensity and texture associated with the points.

17. A non-transitory computer-readable medium that stores a computer program that, when executed by a processor, causes the processor to:
read data corresponding to a three-dimensional region of interest that includes at least one object of interest,
identify a segment of interest corresponding to a contour of the object of interest, by identifying points in the segment of interest having similar characteristics based on the data,
identify a plurality of sub-segments within the segment of interest, boundaries of the sub-segments being based on variations of at least one characteristic within the segment of interest,
remove select sub-segments from the segment of interest to form an other segment of interest corresponding to the contour of the object of interest, and
display the segment of interest, the boundaries of the sub-segments, and the other segment of interest.

18. The medium of claim 17, wherein the boundaries of the sub-segments are determined by determining local minima and watersheds within the segment of interest.

19. The medium of claim 17, wherein the program causes the processor to determine distances of the points in the segment from an edge of the segment to facilitate identifying the boundaries of the sub-segments.

20. The medium of claim 17, wherein the program causes the processor to remove at least one of the select sub-segments based on a surface area of the boundary of the sub-segment.

* * * * *